United States Patent [19]

Teass, Jr.

[11] Patent Number: 4,668,944
[45] Date of Patent: May 26, 1987

[54] FAIL SAFE CIRCUIT FOR A SALINITY MONITOR

[76] Inventor: Horace A. Teass, Jr., 20 N. MacQuesten Pkwy., Mount Vernon, N.Y. 10550

[21] Appl. No.: 812,769

[22] Filed: Dec. 23, 1985

[51] Int. Cl.$^4$ ............................................. G08B 21/00
[52] U.S. Cl. ..................................... 340/603; 324/51; 340/507; 340/652
[58] Field of Search ............... 340/603, 507, 509, 652; 324/51, 439

[56] References Cited

U.S. PATENT DOCUMENTS

| | | | |
|---|---|---|---|
| 2,684,475 | 7/1954 | Lode | 340/593 X |
| 3,521,276 | 7/1970 | Raber | 340/509 |
| 4,181,880 | 1/1980 | Teass, Jr. | 324/439 |
| 4,190,827 | 2/1980 | Diamond | 324/439 X |

Primary Examiner—James L. Rowland
Assistant Examiner—Daniel Myer
Attorney, Agent, or Firm—Peck & Peck

[57] ABSTRACT

A fail safe circuit is provided in a salinity monitor having a salinity indicating panel for visually presenting salinity levels and a salinity cell for sensing salinity levels. The salinity cell is electrically connected to the salinity indicating panel by a plurality of salinity cell leads which supply electrical signals to the salinity indicating panel for indication of salinity levels. The fail safe circuit enables an alarm when a salinity cell lead becomes disconnected from the salinity indicating panel. Also, a back-up circuit is provided for enabling an alarm should the fail safe circuit become inoperative.

4 Claims, 2 Drawing Figures

4,668,944

FAIL SAFE CIRCUIT FOR A SALINITY MONITOR

BACKGROUND OF THE INVENTION

1. Technical Field

The present invention relates to a salinity monitor and, more particularly, to a salinity monitor having a fail safe circuit for enabling an alarm should one or more of the salinity cell leads become disconnected and a back-up circuit for enabling an alarm should the fail safe circuit become inoperative.

2. Discussion of the Prior Art

A conventional salinity monitor monitors the concentrations of salts, or other dissolved solutes in a solution, by measuring the electrolytic conductivity of the solution. Salinity monitors generally include a salinity indicating panel for visually presenting salinity levels and at least one salinity cell. The salinity cell has a plurality of salinity cell leads electrically connected to the salinity indicator panel and provides an electrical signal to the salinity indicating panel proportional to the salinity of the solution. Salinity as used here and throughout the specification is interchangeable with conductivity.

Salinity monitoring is needed in water processing equipment where damage can result to the water processing equipment by water having high salinity levels. Salinity monitors of the type described are represented in U.S. Pat. Nos. 4,190,827, and 4,181,880, and the subject matter described and illustrated in these patents is expressly incorporated herein in its entirety by this reference.

The prior art fails to disclose or suggest the use of a fail safe circuit to enable an alarm should a salinity cell lead become disconnected from the salinity indicating panel. As a consequence, damage may result to water processing equipment should a salinity cell lead become disconnected from the salinity indicating panel.

Conventional salinity monitors, not having circuits to monitor the condition of salinity cell leads, do not indicate by an alarm or other means a disconnect condition of any salinity cell lead.

OBJECTS AND SUMMARY OF THE PRESENT INVENTION

It is therefore an object of the present invention to provide a salinity monitor that will not cause damage to water process equipment as a result of a disconnected salinity cell lead.

Another object of the present invention is to provide a salinity monitor that indicates by an alarm the disconnected condition of any salinity cell lead.

In accordance with the present invention a fail safe circuit is provided in a salinity monitor having a salinity indicating panel for visually presenting salinity levels and a salinity cell for sensing salinity levels. The salinity cell is electrically connected to the salinity indicating panel by a plurality of salinity cell leads which supply electrical signals to the salinity indicating panel for indication of salinity levels. The fail safe circuit enables an alarm when a salinity cell lead becomes disconnected from the salinity indicating panel. Also, a back-up circuit is provided for enabling an alarm should the fail safe circuit become inoperative.

BRIEF DESCRIPTION OF THE DRAWINGS

The above and still further objects, features and advantages of the present invention will become apparent upon consideration of the following detailed description of specific embodiments thereof, especially when considered in conjunction with the accompanying drawings wherein like parts in each of the several figures are identified by the same reference numerals, and wherein.

DESCRIPTION OF THE PREFERRED EMBODIMENTS

Figure 1:
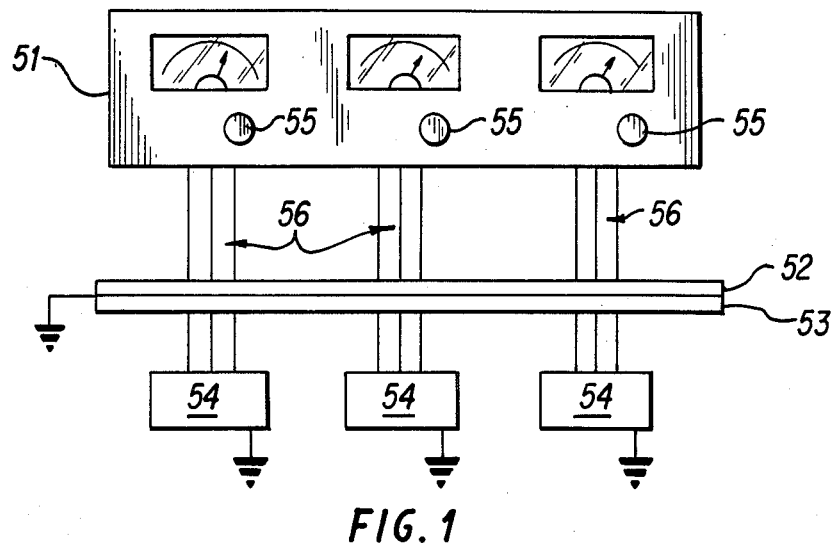
FIG. 1 is a schematic diagram of an embodiment of the salinity monitor.

Referring specifically to the schematic diagram of FIG. 1, the salinity monitor of the present invention includes a salinity indicating panel 51 and a plurality of salinity cells 54, each salinity cell 54 having a plurality of salinity cell leads or electrical leads 56. Each salinity cell lead 56 is electrically connected to the salinity indicating panel 51. The salinity monitor further includes a fail safe circuit represented by the block 52, and a back-up circuit represented by the block 53. An alarm 55 is generally designated by the numeral 55.

The salinity monitor illustrated in FIG. 1 operates as follows. The salinity cell 54 senses salinity levels of a solution and supplies an electrical signal proportional to the salinity of the solution to the salinity indicating panel 51. A fail safe circuit 52 enables an alarm 55 should a salinity cell lead 56 become disconnected from the salinity indicating panel 51.

Figure 2:
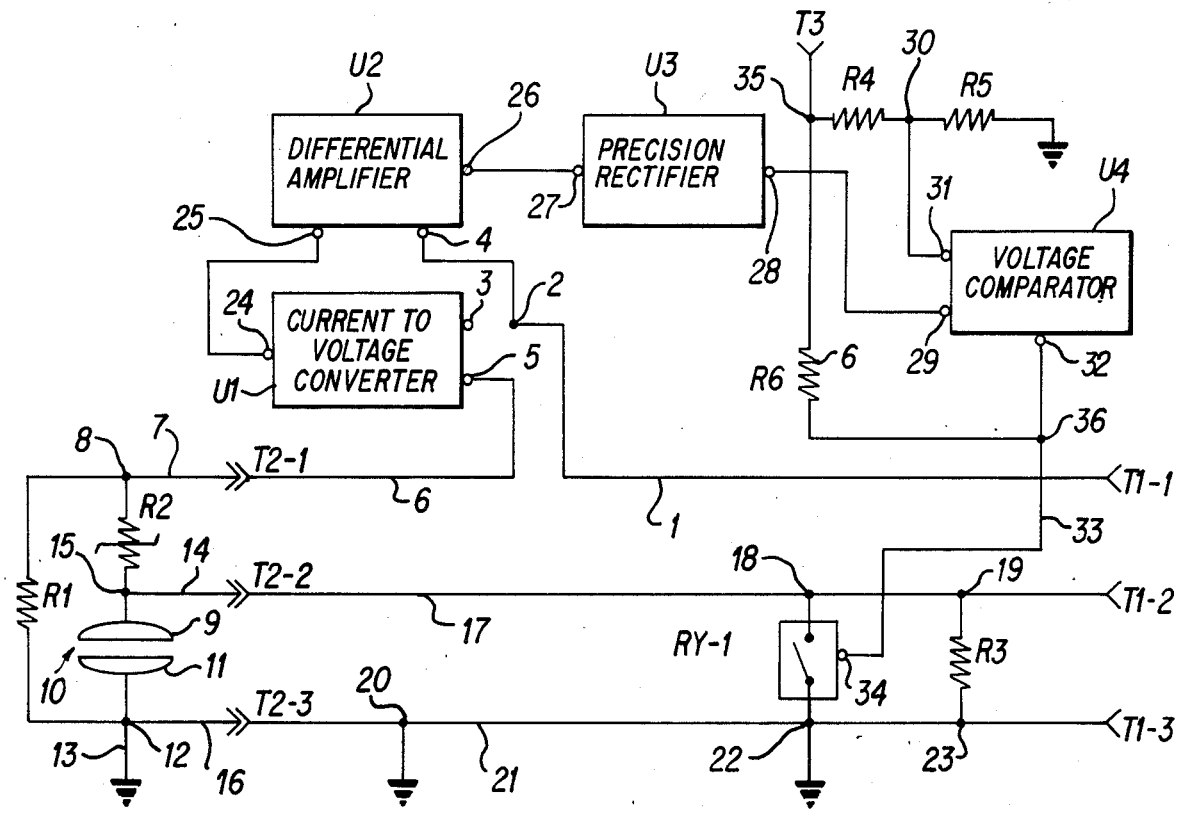
FIG. 2 is a schematic diagram of the embodiment of the fail safe and back-up electrical circuits of the present invention.

Referring specifically to the schematic diagram of FIG. 2, the fail safe circuit and the back-up circuit of the present invention include a current to voltage converter U1 which has a first input terminal 3 electrically connected to a junction point 2 for receiving an a.c. signal from the salinity indicating panel through a terminal T1-1. A second input terminal 5 of the current to voltage converter U1 is electrically connected to a first salinity cell lead 7 through conductor 6. An output terminal 24 of the current to voltage converter U1 is electrically connected to a first input terminal 25 of a differential amplifier U2. First salinity cell lead or first electrical lead 7 is connected to terminal T2-1. The differential amplifier U2 further includes a second input terminal 4 electrically connected to the junction point 2 and an output terminal 26 electrically connected to an input terminal 27 of a precision rectifier U3. The precision rectifier U3 has an output terminal 28 electrically connected to a first input terminal 29 of a voltage comparator U4. The voltage comparator U4 further includes a second input terminal 31 electrically connected to a junction point 30 between two electrically connected resistors R4 and R5, resistor R4 being connected to a regulated voltage at junction point 35 of regulated voltage input terminal T3, and resistor R5 being electrically connected to a ground potential. An output terminal 32 of the voltage comparator U4 is electrically connected to a junction point 36 which is also electrically connected to control terminal 34 of an electronic switch or relay RY-1. The electronic switch RY-1 includes a second switch terminal electrically connected to a junction point 22, which is electrically connected to chassis ground potential 20 through conductor 21, and a third switch terminal which is electrically connected to terminal T2-2 via junction point 18 and conductor 17. Junction point 22 is also electrically connected to a junction point 23 which is electrically connected to terminal T1-3. Junction point 18 is also electrically connected to junction point 19 which is electrically connected to terminal T1-2. Junction point 20 is electrically connected to terminal T2-3. The electronic switch RY-1 is controlled by a high or low voltage on control terminal 34. A resistor R3 is electrically connected between junction points 19 and 23. Terminal T1-2 provides the salinity level indicating signals to the salinity indicating panel. A resistor R6, serving as the back-up circuit, is electrically connected between regulated voltage input terminal T3 and a junction point 36 which is electrically connected to the output terminal 32 of voltage comparator U4.

The salinity cell includes a first salinity cell lead 7, a thermistor R2 electrically connected between the salinity cell lead 7 at a junction point 8 and a junction point 15 which is electrically connected to a first electrode 9. The second salinity cell lead or second electrical lead 14 is electrically connected to the junction point 15. A second electrode 11 is spaced opposite the first electrode 9 and is electrically connected to the third salinity cell lead 16 at junction point 12. A resistor R1 is electrically connected between the first salinity cell lead 7 at junction point 8 and the third salinity cell lead 16 at junction point 12. The third salinity cell lead or third electrical lead 16 is electrically connected to pipe ground potential at junctiopn point 12 through conductor 13. The space represented by 10 between the first and second electrodes 9 and 11 is a path for water of which the salinity level is to be detected.

The fail safe circuit and back-up circuit operates as follows. An a.c. signal from the salinity indicating panel is supplied to the first input terminal 3 of current to voltage converter U1 and to a second input terminal 25 of the differential amplifier U2. The second input terminal 5 receives a current signal from the first salinity cell lead 7. The voltage signal on output terminal 24 of current to voltage converter U1 remains at least 1.2 times greater than the a.c. signal applied at the input terminal 3. The voltage signal at output terminal 24, applied to the first input terminal of differential amplifier U2 along with the a.c. signal at the second input terminal 4, is differentiated by the differential amplifier U2 to provide an a.c. voltage signal at output terminal 26 equal to the difference between the voltage signal from current to voltage converter U1 and the a.c. signal. The output signal from differential amplifier U2 being an a.c. signal is converted to a rectified voltage by precision rectifier U3 and is provided to the first input terminal 29 of voltage comparator U4. Voltage comparator U4 compares the rectified voltage to a reference voltage provided to the second input terminal 31. If the rectified voltage is less than the reference voltage, comparator U4 provides a high voltage at the output terminal 32; if the rectified voltage is greater than the reference voltage, voltage comparator U4 provides a low voltage at output terminal 32. The control signal from output terminal 32, electrically connected to the control terminal 34 of electronic switch RY-1, places electronic switch RY-1 in an open condition if the control signal is a low voltage, and in a closed condition if the control signal is a high voltage.

The fail safe circuit is actuated in two different ways, depending upon the particular salinity cell lead that is disconnected. Should salinity cell lead 7 become disconnected from conductor 6, there is no longer a signal path from the second input terminal 5 to the chassis ground potential junction 22. In this case, the voltage signal at output terminal 24 of the current to voltage converter U1 is no longer 1.2 times greater than the a.c. signal at the first input terminal 3, but instead corresponds to the a.c. signal at input terminal 3. This a.c. signal, being provided to the second input terminal 4 of differential amplifier U2 along with the voltage signal from the output terminal 24, provides a zero volts difference signal at output terminal 26 of the differential amplifier U2. Zero volts provided to the precision rectifier input terminal 27 produces a zero volts output at the output terminal 28. Zero volts at the input terminal 29 of voltage comparator U4 is less than the reference voltage provided to the input terminal 31. As explained earlier, this results in a high voltage control signal at the output terminal 32 of voltage comparator U4. The high voltage control signal from the output terminal 32, combined with the current that passes from junction 35 through resistor R6, closes electronic switch RY-1 through control terminal 34, resulting in a short circuit condition between conductors 17 and 21. The short circuit condition drops the input to the salinity indicating panel, terminal R1-2, to chassis ground potential which is a condition equivalent to a very high salinity level of the water 10 between electrodes 9 and 11. This short circuit condition causes the salinity indicating panel to enable the alarm, notifying the operator of a fault.

For the alarm to be enabled if salinity cell lead 16, which is terminal T2-3, becomes disconnected form conductor 21, it is necessary for the salinity cell to become disconnected from the pipe ground potential through junction point 12 and conductor 13. Further, the alarm will not be enabled if pipe ground potential becomes disconnected and salinity cell lead 16 remains connected to conductor 21. In either case, the salinity indicating panel will operate normally because a ground path still exists. However, should both pipe ground potential and chassis ground potential become disconnected simultaneously, no signal path will exist from the second input terminal 5 of current to voltage converter U1 to chassis ground potential at junction point 22. The result will be identical to that described above when salinity cell lead 7 becomes disconnected from terminal T2-1.

Should salinity cell lead 14 become disconnected from conductor 17, no signal path exists to terminal T1-2 which is the input terminal to the salinity indicating panel. Terminal T1-2 is placed in a short circuit condition to chassis ground potential by conductor 17 and resistor R3. This short circuit condition between conductor 17 and 21 is equivalent to a very high salinity level which causes the salinity indicating panel to enable the alarm notifying the operator of a fault.

Resistor R6 provides the back-up circuit should the fail safe circuit become inoperative. Resistor R6 enables the alarm should any or all of the electrical components U1-U4 become inoperative. Resistor R6, being connected to junction point 36 and regulated voltage input terminal T3, will pull junction point 36 to a high voltage level if there is no voltage signal from output terminal 32 of voltage comparator U4, as when any or all of the electrical components U1-U4 become inoperative. A low voltage from output terminal 32 will pull junction point 36 to a low voltage. The high voltage at junction point 36 caused by resistor R6 provides a high voltage to control terminal 34 of electronic switch RY-1 which places electronic switch RY-1 in a closed condition, thereby causing a short circuit condition between conductors 17 and 21. This short circuit condition is equivalent to a very high salinity level and causes the salinity indicating panel to enable the alarm, notifying the operator of a fault.

Having described a preferred embodiment of a novel salinity monitor in accordance with the present invention, it is believed that other modifications, variations and changes will be suggested to those skilled in the art in view of the teachings set forth herein. It is, therefore, to be understood that all such variations, modifications and changes are believed to fall within the scope of the present invention as defined by the appended claims.

What is claimed is:

1. In a salinity monitor of the type wherein a salinity cell is employed to measure salinity of a liquid and is connected to a salinity indicating panel by means of first, second and third electrical leads, a fail safe circuit comprising:

first means within the salinity cell for generating a current signal, the absence or presence of which represents whether the first and third electrical leads are connected to the salinity indicating panel and a salinity level signal representative of the salinity of the liquid;

second means within the salinity indicating panel for providing an a.c. signal representing a standard signal for comparison to signals provided by the salinity cell;

third means responsive to the a.c. signal and the absence or presence of the current signal for providing an a.c. differential voltage signal having a level which represents whether the first and second electrical leads are connected to the salinity indicating panel;

reference means for providing a reference voltage representing a voltage level below which indicates a disconnected electrical lead and above which indicates a connected electrical leads;

voltage comparator means responsive to the reference voltage and the a.c. differential voltage signal for providing a control signal representing a disconnected electrical lead by a high voltage connected electrical lead by a low voltage;

electronic switch means responsive to the control signal for causing said salinity level signal to indicate a high salinity level thereby enabling an alarm; and circuit means responsive to a disconnected condition of the second electrical lead, said circuit means causing said salinity level signal to indicate a high salinity level thereby enabling an alarm.

2. The fail safe circuit according to claim 1 wherein said third means comprises:

a precision rectifier means for converting said a.c. differential voltage signal to a d.c. voltage signal, said precision rectifier means providing said d.c. voltage signal to said voltage comparator means.

3. The fail safe circuit according to claim 2 wherein said third means further comprises:

a current to voltage converter means responsive to said current signal and said a.c. signal for providing an output signal representing the connected condition of said first and second electrical leads by said output signal having a predetermined factor greater than said a.c. signal; and a differential amplifier means responsive to said output signal and said a.c. signal, for providing a differential voltage signal representing the difference between the a.c. signal and the output signal.

4. The fail safe circuit according to claim 1 further comprising:

a back-up circuit means responsive to the absence of said control signal for enabling an alarm representing the inoperative condition of said fail safe circuit.

* * * * *